(12) United States Patent
Yeh

(10) Patent No.: US 11,554,223 B2
(45) Date of Patent: Jan. 17, 2023

(54) SAFETY NEEDLE AND SAFETY NEEDLE DEVICE

(71) Applicant: CC Biotechnology Corporation, Tainan (TW)

(72) Inventor: Chin-Min Yeh, Tainan (TW)

(73) Assignee: CC Biotechnology Corporation, Tainan (TW)

( * ) Notice: Subject to any disclaimer, the term of this patent is extended or adjusted under 35 U.S.C. 154(b) by 373 days.

(21) Appl. No.: 16/651,448

(22) PCT Filed: Sep. 30, 2017

(86) PCT No.: PCT/CN2017/104828
§ 371 (c)(1),
(2) Date: Mar. 27, 2020

(87) PCT Pub. No.: WO2019/061420
PCT Pub. Date: Apr. 4, 2019

(65) Prior Publication Data
US 2022/0143325 A1 May 12, 2022

(51) Int. Cl.
*A61M 5/32* (2006.01)
*A61M 5/50* (2006.01)
*A61M 5/34* (2006.01)

(52) U.S. Cl.
CPC ............ *A61M 5/3272* (2013.01); *A61M 5/50* (2013.01); *A61M 5/3202* (2013.01); *A61M 5/3213* (2013.01); *A61M 5/347* (2013.01)

(58) Field of Classification Search
CPC .... A61M 5/3272; A61M 5/50; A61M 5/3202; A61M 5/347; A61M 5/32; A61M 5/3243; A61M 5/3257; A61M 2005/3267
See application file for complete search history.

(56) References Cited

U.S. PATENT DOCUMENTS 5,984,899 A 11/1999 D'Alessio et al.
6,248,094 B1 * 6/2001 Epperson .............. A61M 5/322
604/110

(Continued)

FOREIGN PATENT DOCUMENTS

CN 1819852 A 8/2006
CN 202724377 U 2/2013
(Continued)

*Primary Examiner* — Bhisma Mehta
*Assistant Examiner* — Neeraja Gollamudi
(74) *Attorney, Agent, or Firm* — Alan D. Kamrath; Karin L. Williams; Mayer & Williams PC

(57) ABSTRACT

A safety needle (10) and a safety needle device (1). The safety needle device (1) comprises the safety needle (10), an outer protective cover (60), and a sealing membrane (70). The outer protective cover (60) cooperates with the sealing membrane (70) to seal and package the safety needle (10). The safety needle (10) comprises a needle sleeve housing (20), a syringe assembly holder (40), a needle (30), and an elastic safety cover (50). The syringe assembly holder (40) is provided at a rear end of the needle sleeve housing (20). The needle (30) is movably provided inside the needle sleeve housing (20) and the syringe assembly holder (40). The elastic safety cover (50) is provided in the needle sleeve housing (20) so as to be capable of rotating and extending and retracting. A non-return guide slot (23) having a non-return elastic plate (235) in the needle sleeve housing (20) guides a needle sheath elastic engagement component (55) of a needle sheath (51) of the elastic safety cover (50) such that the elastic safety cover (50) can extend and retract in an axial direction of the needle sleeve housing (20) and control the timing of the extension of the needle (30) outside the elastic safety cover (50). After use, the elastic safety cover (50) covering an outer side of the needle (30) can be stopped and locked in the needle sleeve housing (20) by the non- (Continued)

return elastic plate (235) such that the safety needle (10) cannot be used again, thus ensuring safety of use.

13 Claims, 12 Drawing Sheets

(56) References Cited

U.S. PATENT DOCUMENTS

| | | | |
|---|---|---|---|
| 7,922,698 B2 | 12/2011 | Riesenberger et al. | |
| 9,078,978 B2 | 7/2015 | Schraga | |
| 9,770,200 B2 | 9/2017 | Schraga | |
| 9,962,497 B2 | 5/2018 | Takemoto | |
| 10,022,505 B2 | 7/2018 | Hu | |
| 10,463,809 B2 | 11/2019 | Takemoto | |
| 10,537,688 B2 | 1/2020 | Wittland et al. | |
| 2005/0113750 A1 | 5/2005 | Targell | |
| 2009/0118676 A1* | 5/2009 | Emmott | A61M 5/002 604/195 |
| 2012/0041368 A1* | 2/2012 | Karlsson | A61M 5/326 604/111 |
| 2012/0316508 A1* | 12/2012 | Kirchhofer | A61M 5/31553 604/198 |
| 2013/0172818 A1 | 7/2013 | Schraga | |
| 2018/0021524 A1* | 1/2018 | Takemoto | A61M 5/3271 604/198 |

FOREIGN PATENT DOCUMENTS

| | | |
|---|---|---|
| CN | 203524683 U | 4/2014 |
| CN | 104619366 A | 5/2015 |
| CN | 204395141 U | 6/2015 |
| CN | 107206187 A | 9/2017 |
| TW | 201729856 A | 9/2017 |
| WO | WO2016202614 A1 | 12/2016 |
| WO | WO2017147817 A1 | 9/2017 |

* cited by examiner

SAFETY NEEDLE AND SAFETY NEEDLE DEVICE

BACKGROUND OF THE INVENTION

1. Field of the Invention

The present invention relates to a safety needle, and more particularly to a safety needle and a safety needle device that is connected to a front end of a syringe to inject medicine.

2. Description of Related Art

To reduce the risk of a medical staff being infected by accidental needle stick injuries during an injection process to a patient, a safety needle is used. A conventional safety needle comprises a needle assembly and an outer cap mounted around the needle assembly. Before injection, a needle of the needle assembly is kept from exposure by the outer cap mounted around the needle assembly.

The aforementioned conventional safety needle can provide a safety effect by the outer cap mounted around the needle assembly, and the needle may also be exposed during the transportation and use of the conventional safety needle. Additionally, a user cannot recognize a conventional safety needle being used or not by its appearance, a used safety needle may be misused again.

To solve the problems of the conventional safety needle, another conventional safety needle has functions of safety effect and recognition of being used or not. The conventional safety needle comprises a needle mounted on a front end of a needle base and an outer cap mounted around the front end of the needle base. The outer cap has a needle cap provided with a resilient member extending into the needle base, and the needle cap has a guiding block formed on a rear end of the needle cap and extending into a guiding recess defined in the needle base. With a straight segment, a guiding segment, and a locking segment of the guiding recess, a guiding effect is provided to the guiding block on the rear end of the needle cap. After the safety needle is connected with a syringe and before the injection, the needle cap of the outer cap is mounted around the needle. During the injection, the needle cap can be moved into the needle base to expose the needle. After the injection, the needle cap is pushed to move out of the needle base and covers the needle by the force provided by the resilient member, and the guiding block moves the locking segment of the guiding recess. Consequently, the needle cap cannot be moved into the needle base again to ensure that the needle is held inside the needle cap and the safety needle cannot be used again. Accordingly, the conventional safety needle can be recognized as used.

However, the conventional safety needle has functions of safety effect and recognition of being used or not, but the guiding recess composed of the straight segment, guiding segment, and the locking segment does not have a check effect to the guiding block while the guiding block moves along the guiding recess to the locked position in the locking segment. The needle cap may be moved backward due to an external force, such that the locking capability and safety effect of the convention safety needle are insufficient.

SUMMARY OF THE INVENTION

The main objective of the invention is to provide a safety needle and a safety needle device to solve the problems of the insufficient locking capability and safety effect of the conventional safety needle.

The present invention provides a safety needle comprising:
  a needle housing comprising
    a casing having
      a movement space;
      an outer wall formed around the movement space and having a rear board; and
    at least one guiding check channel formed in the casing and each one of the at least one guiding check channel comprising
      a start segment located at a front segment of the casing and having a rear end;
      a locking segment located at the front segment of the casing and a side of the start segment;
      an end segment located at a rear segment of the casing and having a front end, a middle connected with the rear end of the start segment, and a check tab formed on and protruding forward from a side of the end segment opposite the start segment and having a free front end extending to a rear end of the locking segment; and
      an inclined guiding segment connected between the locking segment and the front end of the end segment, wherein the free front end of the check tab extends to a side of the inclined guiding segment; and
  a needle connection portion disposed in the movement space, protruding forward from the rear board, and having a needle assembling hole defined axially through the needle connection portion and the rear board;
  a syringe connection base connected with a rear end of the needle housing;
  a needle mounted in the needle assembling hole in the needle connection portion of the needle housing and having a front end extending out of a front end of the needle housing and a rear end extending into the syringe connection base; and
  a safety cap mounted axially moveably and rotatably in the needle housing and comprising
    a needle cap having at least one resilient block formed on a rear end of the needle cap and extending respectively into the at least one guiding check channel in the needle housing;
    a positioning portion mounted in the movement space in the needle housing and connected with the rear board; and
    a resilient member connected between the needle cap and the positioning portion and mounted around the needle connection portion, wherein the safety cap is capable of axially telescopically moving in the needle housing to control the needle to extend out of the safety cap and to lock the safety cap in the needle housing.

Wherein, the needle housing has at least one L-shaped inner channel defined in an inner surface of a front end of the casing, and each one of the at least one L-shaped inner channel extends from the front end of the casing to a position being adjacent to the start segment of one of the at least one guiding check channel; and the at least one resilient block on the needle cap of the safety cap is capable of entering respectively into the start segment of the at least one guiding check channel via the at least one L-shaped inner channel from the front end of the needle housing to make the at least one resilient block generate a pre-rotation resilient force.

Wherein, two fan-shaped recesses are defined in a front side of the rear board of the needle housing, are disposed around the needle connection portion, and are diametrically opposite each other;

at least one through channel is defined in a rear segment of the casing between the at least one guiding check channel and the rear board, and each one of the at least one through channel has a resilient hook protruding rearward from a front inner surface of the through channel and providing a limiting effect to the positioning portion of the safety cap; and the resilient member between the needle cap and the positioning portion is spiral in shape, and the positioning portion has two limiting protrusions extending respectively into the fan-shaped recesses in the rear board of the needle housing to limit a rotation range of the safety cap by the fan-shaped recesses.

Wherein, each one of the at least one guiding check channel further has an opening space located at a side of the check tab and communicating with the locking segment; and the check tab of each one of the at least one guiding check channel has an abutment portion formed on the free front end of the check tab.

Wherein, the needle is connected with a needle positioning plug and is mounted in the needle connection portion of the needle housing; and the rear end of the needle is connected with a needle securing plug and is mounted in the syringe connection base.

Wherein, the rear board of the needle housing has an alignment protrusion formed on a rear side of the rear board;

the needle connection portion of the needle housing has an engaging recess formed in an inner surface of a rear segment of the needle assembling hole; and the syringe connection base comprises
a base body having a rear opening;
a front board having two alignment recesses defined in a front side of the front board and corresponding respectively to the alignment protrusions on the rear board of the needle housing;
a connection tube protruding from a front side of the front board, extending through the rear board and into the needle connection portion and having an engaging flange formed on an outer surface of the connection tube and engaged with the engaging recess; and
a needle through hole defined axially through the connection tube and the front board.

The present invention also provides a safety needle device comprising
an aforementioned safety needle;
an outer cap being hollow, mounted around the safety needle, and having a closed front end and an open rear end; and
a sealing film attached to the open rear end of the outer cap to seal the safety needle inside the outer cap.
Wherein, the outer cap has
at least one rib formed on and axially extending from an inner surface of a front segment of the outer cap; and
at least one engagement protrusion formed on an inner surface of the open rear end of the outer cap;
the needle cap has at least one assembling recess longitudinally defined in an outer surface of the needle cap and engaged respectively with the at least one rib on the outer cap;
the syringe connection base has at least one L-shaped outer channel defined in an outer surface of the syringe connection base; and
the outer cap is positioned by the engagement of the at least one engagement protrusion and the at least one L-shaped outer channel.

Wherein, the outer cap has an annular flange radially formed on an outer surface of the outer cap and attached to the sealing film.

The advantages of the present invention are as follows. The needle is mounted through the needle housing and the syringe connection base. The safety cap can telescopically move and rotate relative to the needle housing. The casing of the needle housing has a guiding check channel. The needle cap of the safety cap has a resilient block extending into the guiding check channel. With the guiding effect of the guiding check channel to the resilient block, the safety cap can be telescopically moved relative to the needle housing, and the time of the needle extending out of the safety cap can be controlled. After use, the safety cap can enclose the needle with the resilient force by the resilient member. The resilient block enters into the locking segment via the check tab and the inclined guiding segment. With the abutment of the check tab with the resilient block, the needled cap can be kept from being moved in reverse. The safety cap is completely locked in the needle housing, and the safety needle cannot be used again.

In addition, the safety needle in accordance with the present invention further has an L-shaped inner channel. The L-shaped inner channel extends from the front opening of the casing to a position being adjacent to the start segment of the guiding check channel. The resilient block on the needled cap can enter the start segment from the L-shaped inner channel, and the resilient member generates a pre-force.

The safety needle device in accordance with the present invention can completely pack the safety needle inside the outer cap with the sealing film to ensure the safety needle device fit with the requirements for safety and hygiene. At this time, the outer cap is mounted around the safety needle. A user is kept from being in contact with the needle while a syringe is connected with the safety needle. Before injection, the safety needle is pulled out of the outer cap by the syringe.

Furthermore, in the safety needle device in accordance with the present invention, the outer cap can keep enclosing the safety needle before the outer cap is being removed from the syringe connection base. The engagement protrusion on the outer cap is engaged with the L-shaped outer channel in the syringe connection base. The rib on the outer cap is engaged with the assembling recess in the needle cap, and the safety needle is held in position inside the outer cap. Before the resilient block on the safety cap enters into the start segment of the guiding check channel via the L-shaped inner channel, the safety needle can be prevented from failure due to wrong starting position. Before the injection, the outer cap mounted around the safety needle is rotated, and the engagement protrusion on the outer cap is disengaged from the L-shaped outer channel in the syringe connection base to detach the outer cap from the safety needle.

In addition, the rib on the outer cap can drive the needle cap to rotate, and the resilient block on the needle cap can enter the start segment of the guiding check channel via the L-shaped inner channel. Accordingly, the positioning portion of the safety cap keeps stationary, and the needle cap is rotated. Thus, the resilient member can generate a pre-force due to rotation and compression.

REFERENCED NUMERALS

| 10 | safety needle | | |
|---|---|---|---|
| 20 | needle housing | 21 | casing |
| 211 | movement space | 212 | outer wall |
| 213 | front end | 214 | rear board |
| 2141 | alignment protrusion | 2142 | fan-shaped recess |
| 215 | L-shaped inner channel | 22 | needle connection portion |
| 221 | needle assembling hole | 222 | engaging recess |
| 23 | guiding check channel | 231 | start segment |
| 232 | locking segment | 233 | end segment |
| 234 | guiding check segment | 235 | check tab |
| 2351 | abutment portion | 236 | opening space |
| 24 | through channel | 25 | resilient hook |
| 30 | needle | 31 | needle positioning plug |
| 32 | needle securing plug | | |
| 40 | syringe connection base | 41 | base body |
| 411 | L-shaped outer channel | 42 | front board |
| 421 | alignment recess | 43 | connection tube |
| 431 | engaging flange | 44 | needle through hole |
| 50 | safety cap | 51 | needle cap |
| 511 | needle hole | 512 | assembling recess |
| 52 | resilient member | 53 | positioning portion |
| 54 | limiting protrusion | 55 | resilient block |
| 60 | outer cap | 61 | rib |
| 62 | engagement protrusion | 63 | annular flange |
| 70 | sealing film | | |
| 80 | syringe | | |

DETAILED DESCRIPTION OF PREFERRED EMBODIMENT

Other objects, advantages and novel features of the invention will become more apparent from the following detailed description when taken in conjunction with the accompanying drawings.

Figure 1:
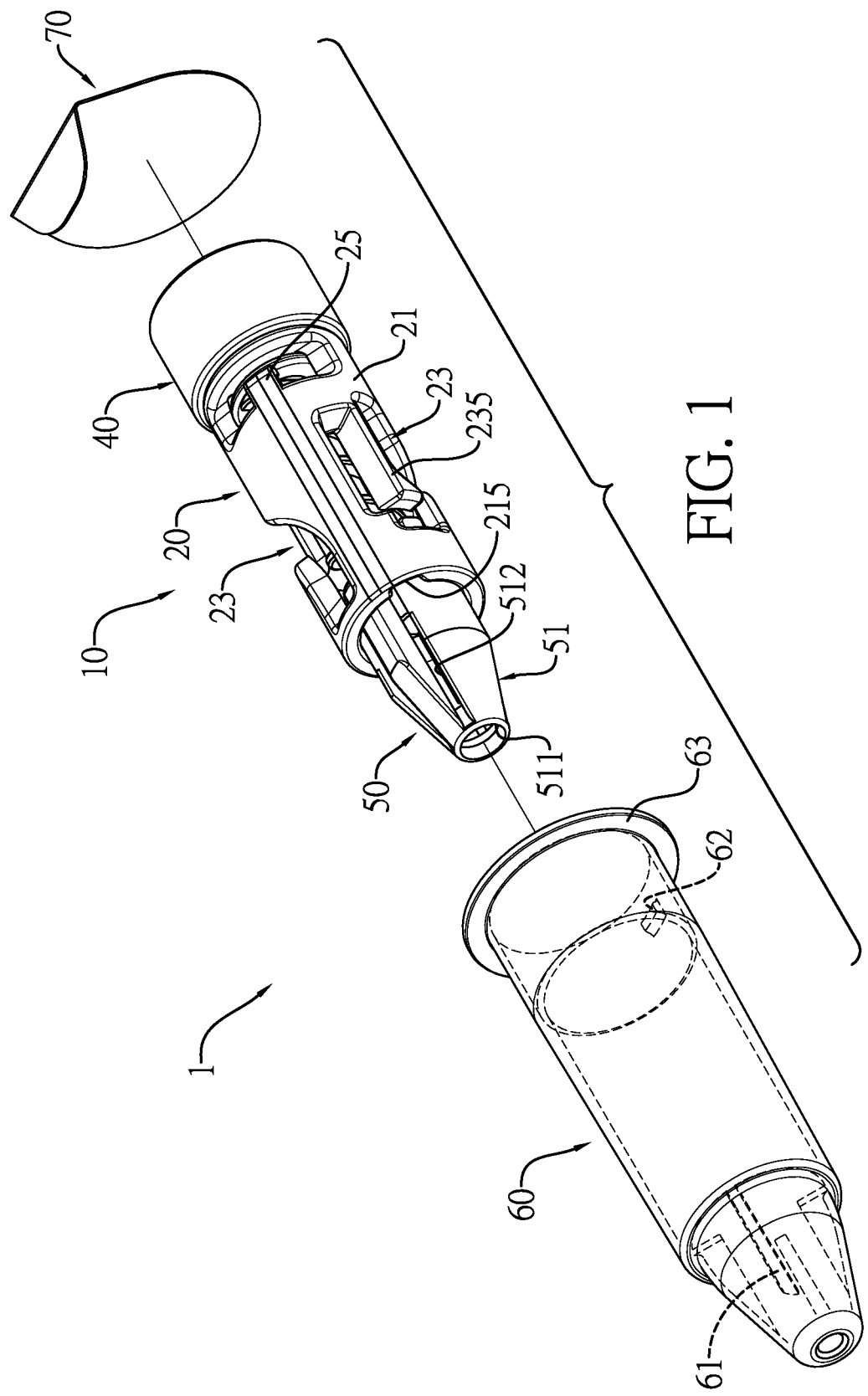
FIG. 1 is an exploded perspective view of a safety needle device in accordance with the present invention.
Figure 2:
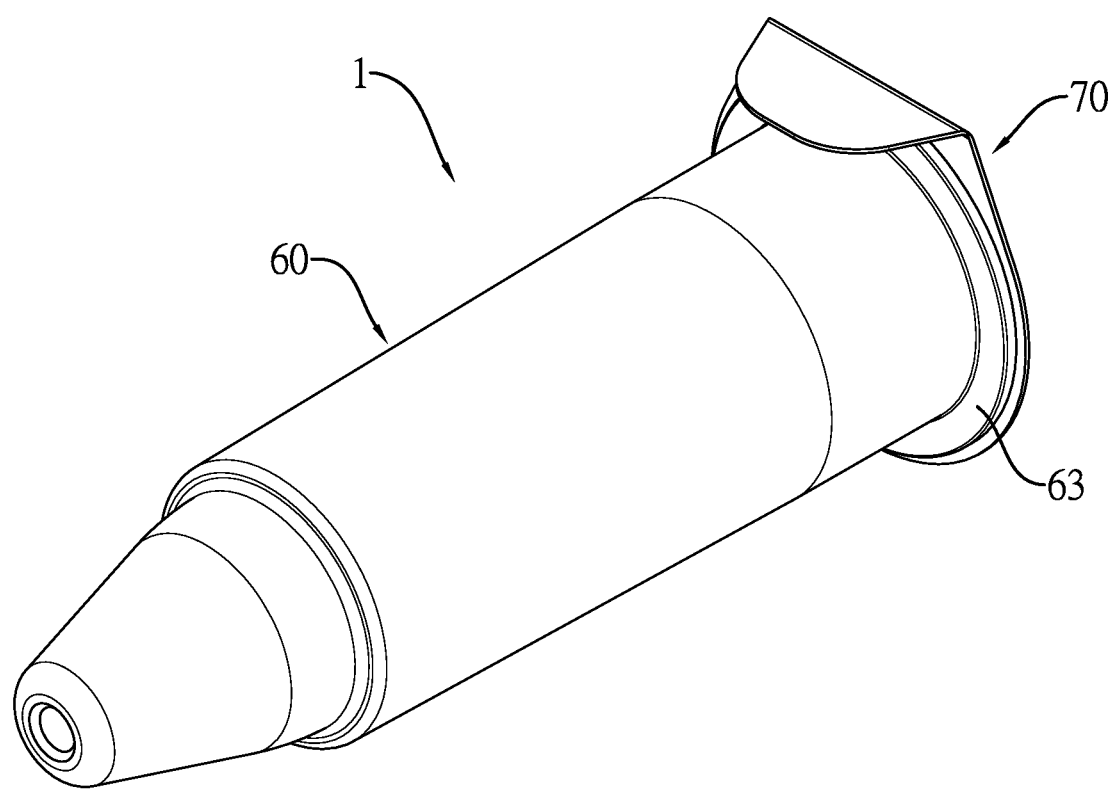
FIG. 2 is a perspective view of the safety needle device in FIG. 1.
Figure 3:
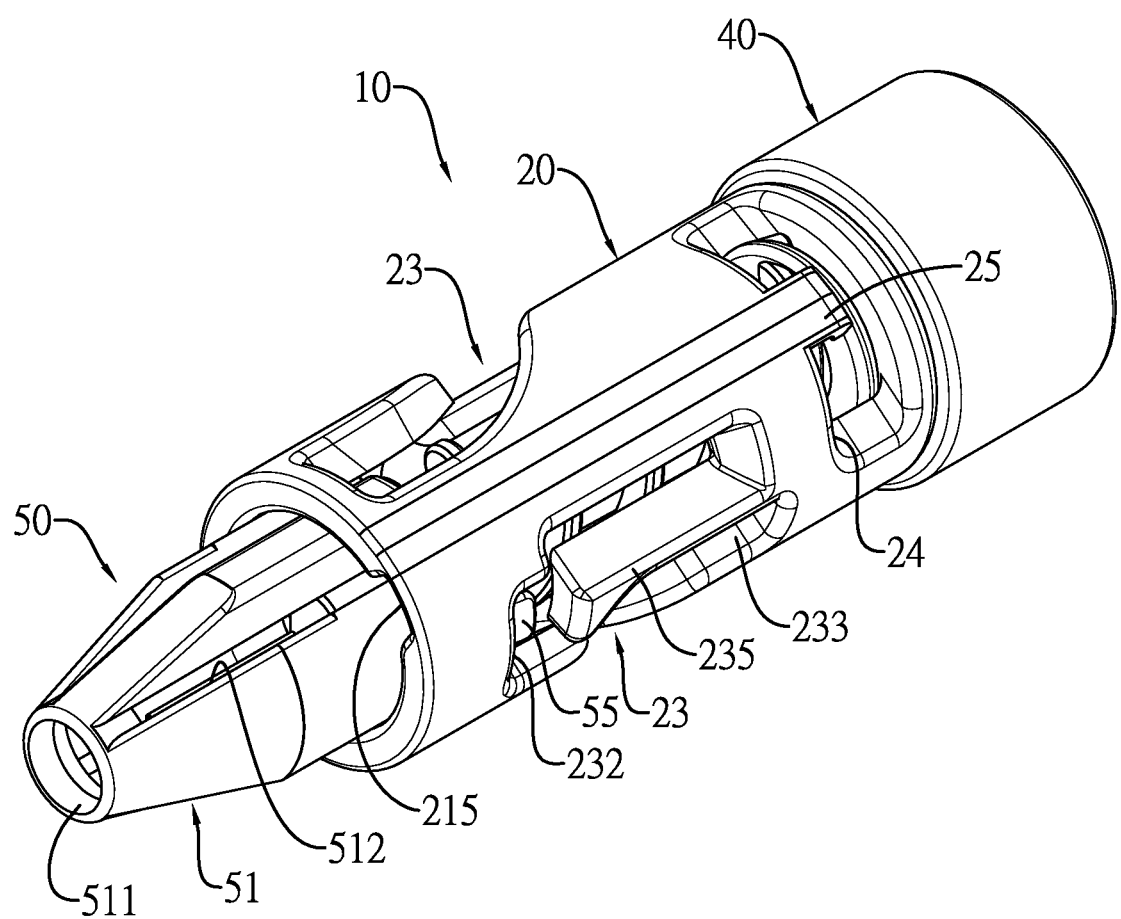
FIG. 3 is a perspective view of a safety needle in accordance with the present invention.
Figure 4:
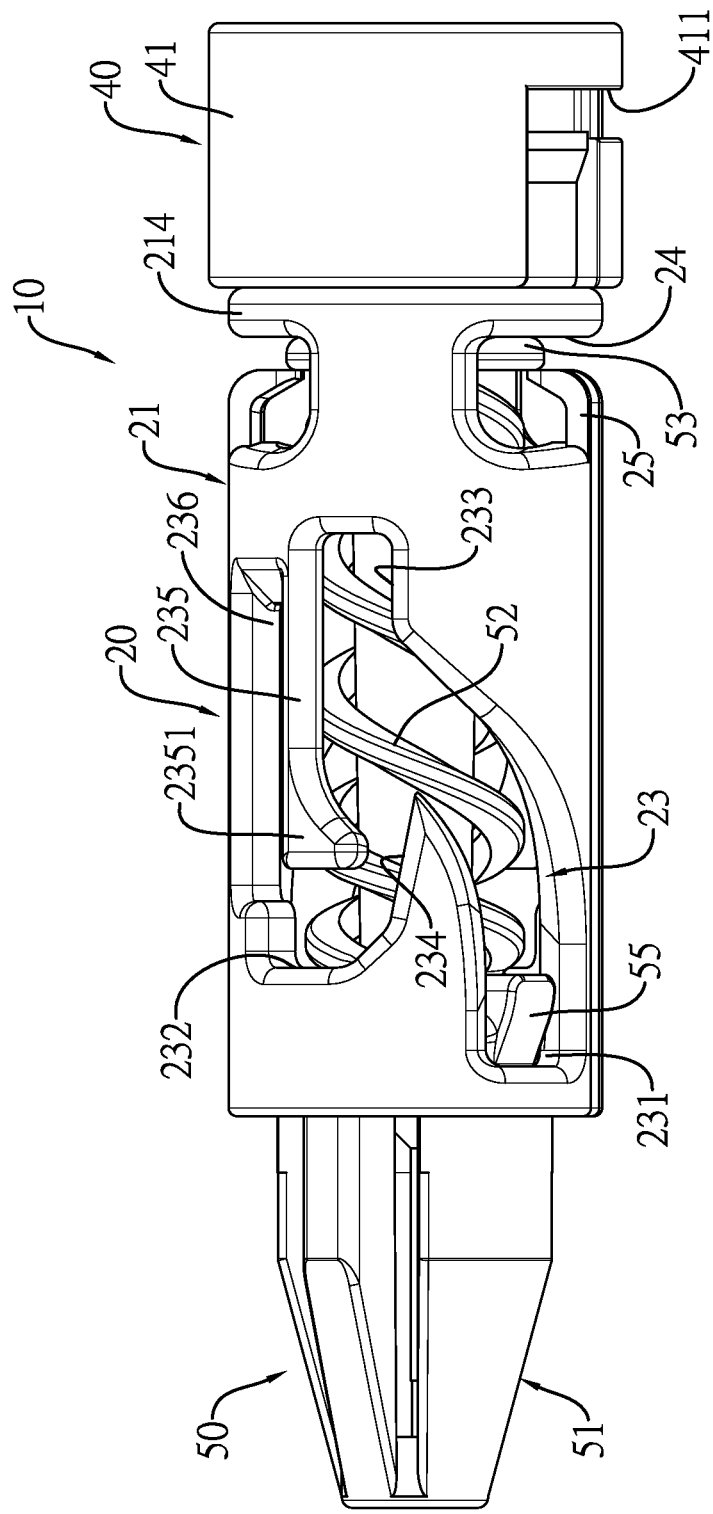
FIG. 4 is a side view of the safety needle in FIG. 3.

The present invention provides a safety needle and a safety needle device. FIGS. 1 and 2 show a preferred embodiment of a safety needle device 1 in accordance with the present invention. FIG. 3 shows a preferred embodiment of a safety needle 10 in accordance with the present invention. The safety needle 10 in accordance with the present invention can be individually packed to ensure the safety thereof, or the safety needle 10 can be applied to the safety needle device 1 as shown in FIG. 1.

With reference to FIGS. 1 and 2, the safety needle device 1 comprises a safety needle 10, an outer cap 60, and a sealing film 70. The outer cap 60 is hollow, is mounted around the safety needle 10, and has a closed front end and an open rear end. The sealing film 70 is attached to the open rear end of the outer cap 60 to seal the safety needle 10 inside the outer cap 60.

In the safety needle device 1 as shown in FIG. 2, at least one rib 61 is formed on and axially extends from an inner surface of a front segment of the outer cap 60, and at least one engagement protrusion 62 is formed on an inner surface of the open rear end of the outer cap 60. The at least one rib 61 and the at least one engagement protrusion 62 are applied to hold the safety needle in position. The outer cap 60 further has an annular flange 63 radially formed on an outer surface of the outer cap 60 and attached to the sealing film 70.

In the safety needle 10 as shown in FIGS. 3 to 7, the safety needle 10 comprises a needle housing 20, a syringe connection base 30, and a safety cap 50 or further comprises a needle positioning plug 31 and a needle securing plug 32.

With reference to FIGS. 3 to 10, the needle housing 20 comprises a casing 21 and a needle connection portion 22. The casing 21 comprises a movement space 211 and an outer wall 212 formed around the movement space 211. The movement space 212 has a front opening 213 formed in a front end of the outer wall 212, and a rear board 214 is formed on a rear end of the outer wall 212. The needle connection portion 22 is disposed in the movement space 211 of the casing 21, protrudes forward from a front side of the rear board 213, and extends to the front opening 213. A needle assembling hole 221 is defined axially through the needle connection portion 22 and the rear board 214. An engaging recess 222 is formed in an inner surface of a rear segment of the needle assembling hole 221.

Figure 7:
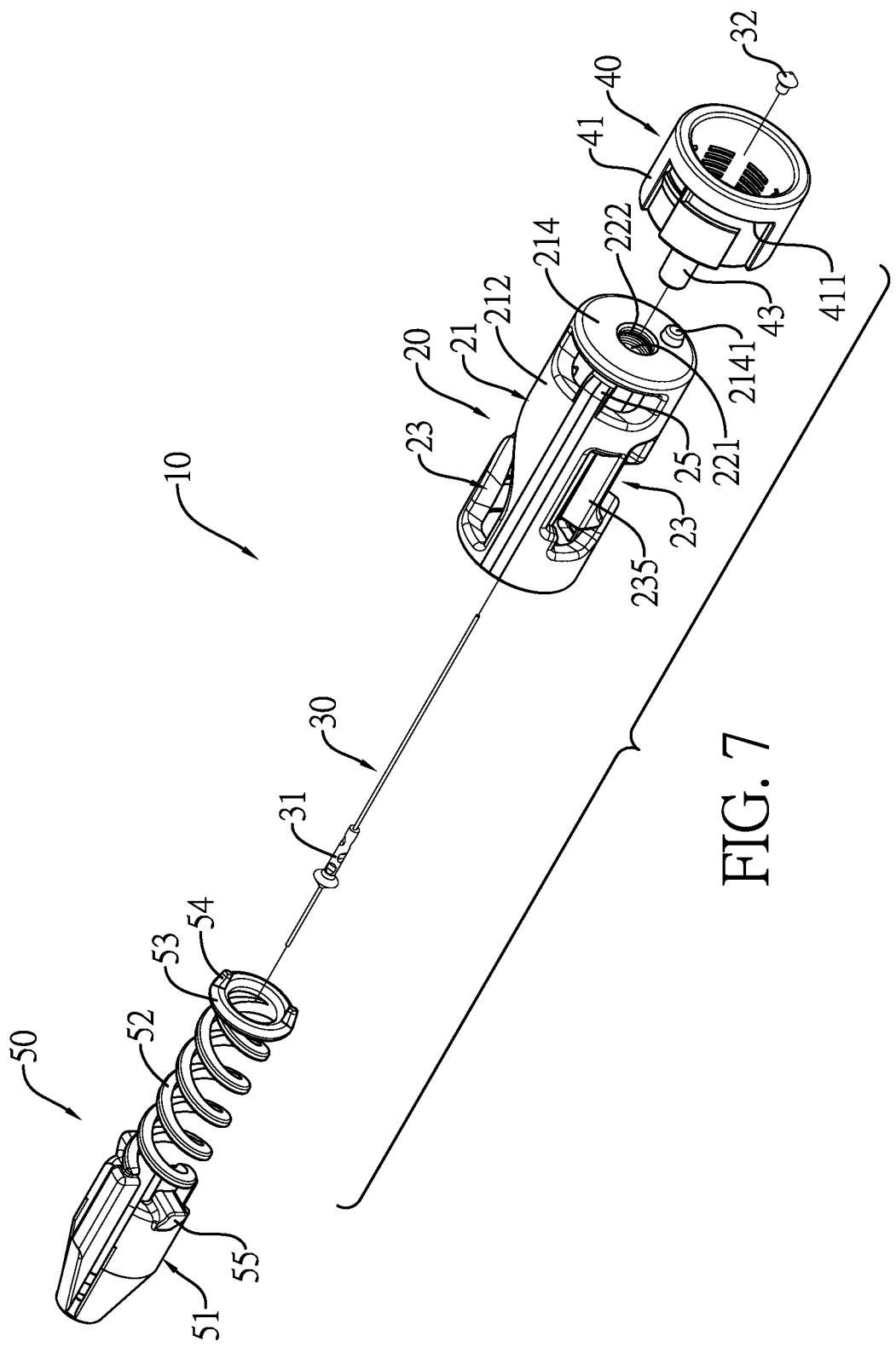
FIG. 7 is another exploded perspective view of the safety needle in FIG. 3.
Figure 8:
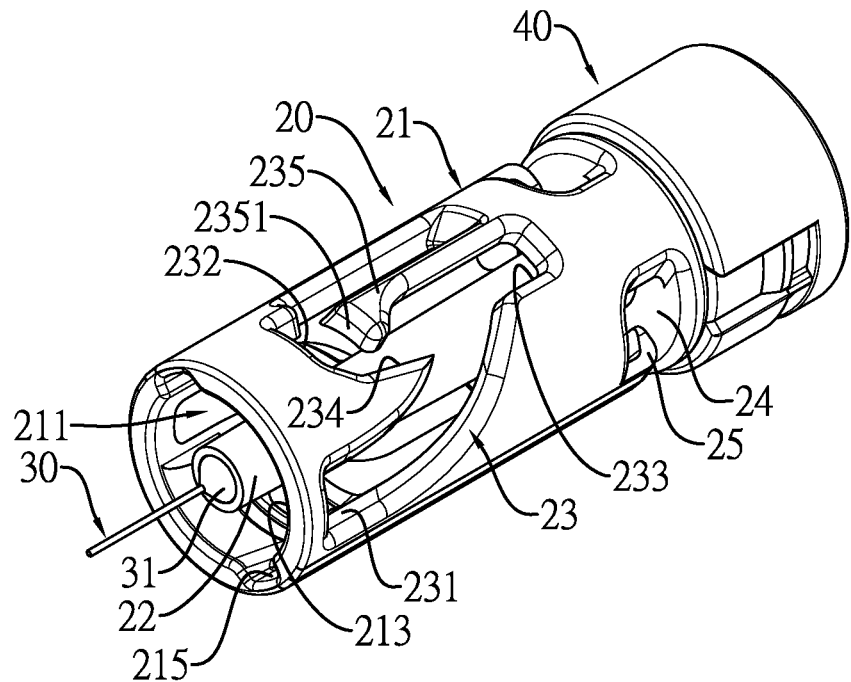
FIG. 8 is a perspective view of the safety needle in FIG. 3 with the safety cap being removed.
Figure 9:
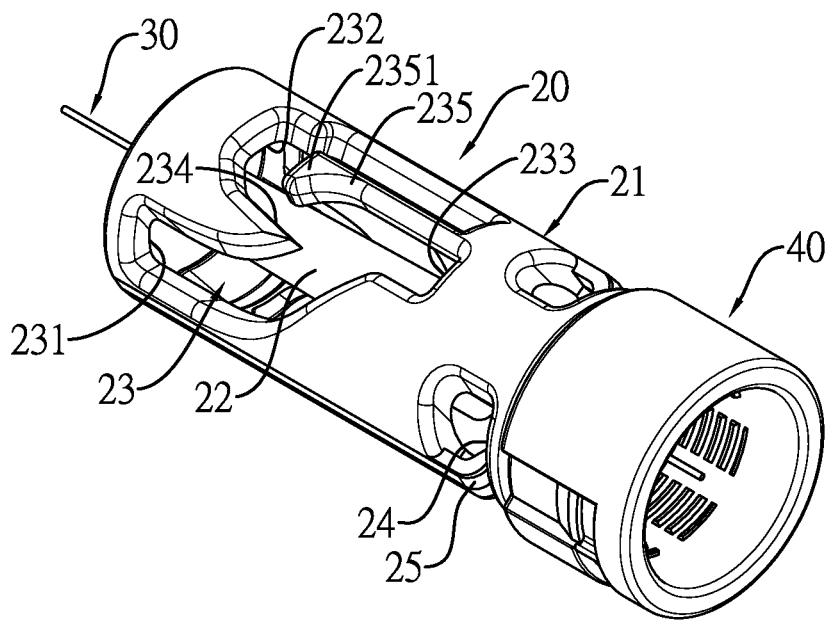
FIG. 9 is another perspective view of the safety needle in FIG. 3 with the safety cap being removed.
Figure 10:
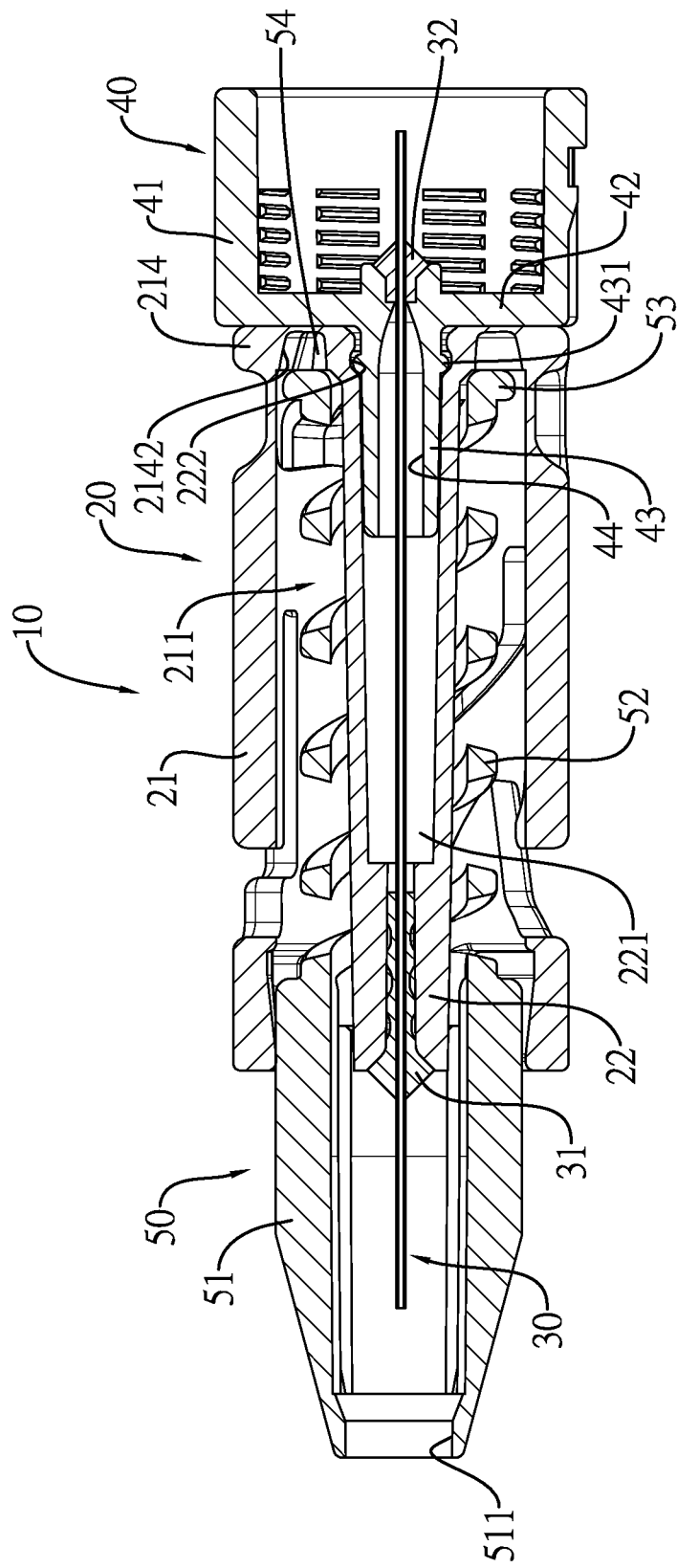
FIG. 10 is a cross sectional side view of the safety needle in FIG. 3.

With reference to FIGS. 7 and 10, in the needle housing 20, an alignment protrusion 2141 is formed on a rear side of the rear board 214 opposite the needle assembling hole 221, and two fan-shaped recesses are defined in the front side of the rear board 214 and are disposed around the needle connection portion 22 and diametrically opposite each other.

With reference to FIGS. 3 to 9, in the needle housing 20, at least one guiding check channel 23 is defined in the casing 21. In this embodiment, two guiding check channels 23 diametrically opposite each other are formed in the casing 21. Each guiding check channel 23 comprises a start segment 231, a locking segment 232, an end segment 233, and an inclined guiding segment 234. The start segment 231 is located at a front segment of the casing 21. The locking segment 232 is located at the front segment of the casing 21 and a side of the start segment 231. The end segment 233 is located at a rear segment of the casing 21 and a side of the start segment 231 and communicates with the start segment 231. The inclined guiding segment 234 is connected between a front end of the locking segment 232 and a front end of the end segment 233. The start segment 231 has a curved rear segment and communicates with a middle of the end segment 233. A check tab 235 is formed on and protrudes forward from a side of the end segment 233 opposite the start segment 231. The check tab 235 has a free front end extending to a rear end of the locking segment 232 and a side of the inclined guiding segment 234. In the preferred embodiment, an opening space 236 is located at a side of the check tab 235 and communicating with the locking segment 232. An abutment portion 2351 is formed on the free front end of the check tab 235.

Figure 5:
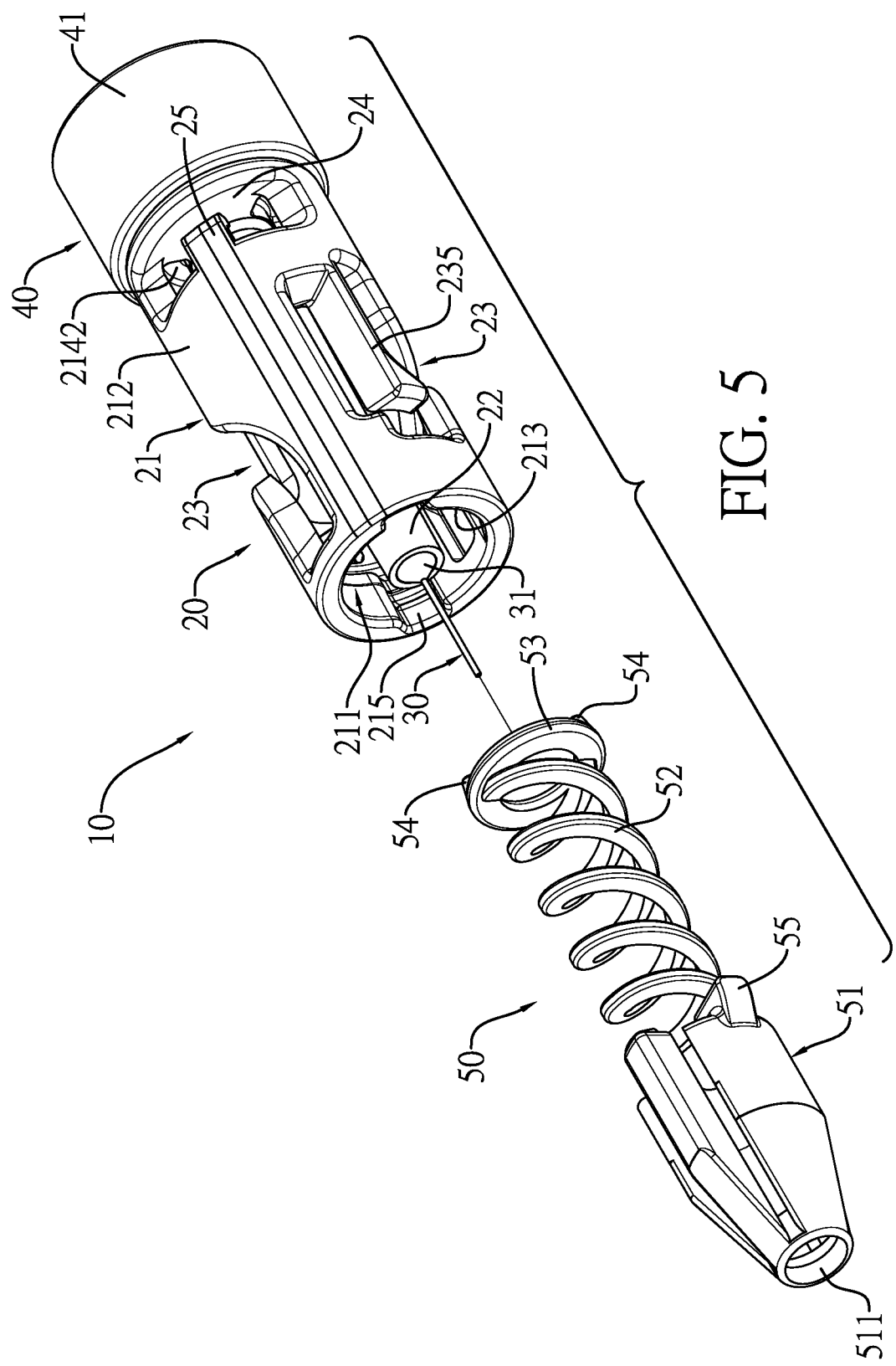
FIG. 5 is an exploded perspective view of the safety needle in FIG. 3 showing a safety cap being departed.
Figure 6:
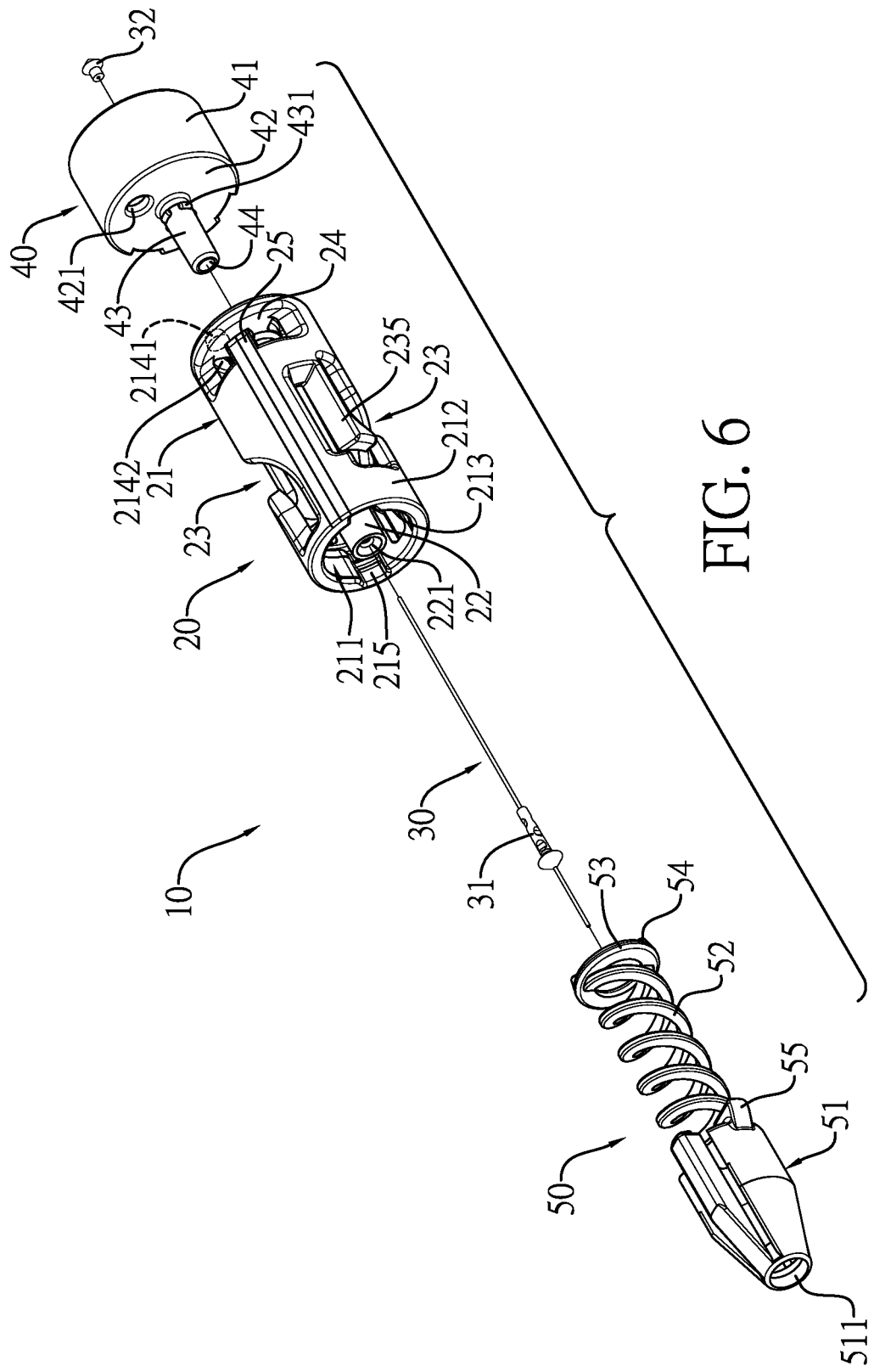
FIG. 6 is an exploded perspective view of the safety needle in FIG. 3.

With reference to FIGS. 5 and 6, the casing 21 further has at least one L-shaped inner channel 215 defined in an inner surface of a front end of the casing 21 and extending from the front opening 213 of the casing 21 to a position being adjacent to the start segment 231 of one of the at least one guiding check channel 23.

With reference to FIGS. 3 to 9, in the needle housing 20, at least one through channel 24 is defined in a rear segment of the casing 21 between the at least one guiding check channel 23 and the rear board 24. The at least one through channel 24 is radially defined through the outer surface of the casing 21 and communicates with the movement space 211. Each through channel 24 has a resilient hook 25 protruding rearward from a front inner surface of the through channel 24. In the preferred embodiment, the casing 21 has two through channels 24 diametrically opposite each other. Each through channel 24 is located between the two guiding check channels 23.

With reference to FIGS. 6 and 7, the syringe connection base 40 is connected with the rear end of the needle housing 20 to connect with a syringe. In the preferred embodiment, the syringe connection base 40 comprises a base body 42 having a rear opening. A front board 42 is formed on a front end of the base body 41, and a connection tube 43 protrudes from a front side of the front board 42. The syringe connection base 40 further has a needle through hole 44 defined axially through the connection tube 43 and the front board 44. The connection tube 43 is mounted through the rear board 214 of the needle housing 20 and into the needle connection portion 22. An alignment recess 421 is defined in a front side of the front board 42 and corresponding to the alignment protrusion 2141 on the rear board 214 of the needle housing 20. An engaging flange 431 is formed on an outer surface of the connection tube 43 and is engaged with the engaging recess 222 in the needle connection portion 22. The base 41 may further have protruding patterns formed on an inner surface thereof to hold the syringe in position. The syringe connection base 40 may further have at least one L-shaped outer channel 411 defined in an outer surface of the syringe connection base 40 to connect with the engagement protrusion 62 on an inner surface of the rear end of the outer cap 60.

With reference to FIGS. 5 to 10, the needle 30 is connected with the needle connection plug 31 and is mounted in the needle assembling hole 221 in the needle connection portion 22 of the needle housing 20. The needle 30 has a front end extending out of the front end of the needle housing 20 and a rear end extending into the base body 41 via the needle through hole 44 of the syringe connection base 40. In the preferred embodiment, the needle combined with the needle positioning plug is mounted in the needle connection portion. A needle securing plug 32 is mounted in the needle through hole 44 in the syringe connection base 40, and the rear end of the needle 30 extends through the needle securing plug 32 to hold the needle 30 inside the needle connection portion 22 and the syringe connection base 40 in position.

With reference to FIGS. 5 to 10, the safety cap 50 is mounted axially moveably and rotatably in the needle housing 20. Before use, the safety cap 50 can enclose the needle 30 inside to prevent the needle 30 from being exposed. During the use, the safety cap 50 can be retracted into the needle housing 20 to extend the needle 30 out of the front end of the safety cap 50. After used, the safety cap 50 encloses the needle 30 inside and is locked in the needle housing 20.

With reference to FIGS. 5 to 7 and 10, the safety cap 50 comprises a needle cap 51, a resilient member 52, and a positioning portion 53. The needle cap 51 and the positioning portion 53 are spaced from each other. The resilient member 52 is connected between the needle cap 51 and the positioning portion 53. The positioning portion 53 is disposed in the movement space 211 of the needle housing 20 and is connected with the rear board 214. Two limiting protrusions 54 are formed on the rear side of the positioning portion 53 and extend respectively into the fan-shaped recesses 2142 in the rear board 214 of the needle housing 20 to limit a rotation range of the safety cap 50 by the fan-shaped recesses 2142.

With reference to FIGS. 5 to 7 and 10, the resilient member 52 can be deformed axially. In the preferred embodiment, the resilient member 52 is spiral in shape and is mounted around the needle connection portion 22 to enable the needle cap 51 of the safety cap 50 to telescopically move and to rotate relative to the front end of the casing 21 of the needle housing 20. The needle cap 51 has a needle hole 511 defined axially through the needle cap 51. At least one assembling recess 512 is longitudinally defined in an outer surface of the needle cap 51 and is engaged respectively with the at least one rib 61 on the outer cap 60. At least one resilient block 55 is formed on a rear end of the needle cap 51 and extends respectively into the at least one guiding check channel 23 in the needle housing 20. With the guiding effect provided by the guiding check channel 23 to the resilient block 55, the safety cap 50 can rotate in a limited range and be locked during the movement of the safety cap 50 relative to the needle housing 20.

With reference to FIGS. 1 to 3 and 11, before the safety needle device 1 is in use, the safety needle 10 is disposed inside the outer cap 60 and the sealing film 70 seals the rear open end of the outer cap 60. The safety needle 10 can be sealed and can be prevented from being polluted to ensure the safety and hygiene of use of the safety needle 10. When the safety needle 10 is in use, the sealing film 70 is departed, and the front end of the syringe 80 is inserted into the syringe connection base 40 of the safety needle 10 held in the outer cap 60, and the rear end of the needle is pierced into the syringe 80. During the connection of the syringe 80 with the safety needle 10, the outer cap 60 keeps enclosing the safety needle 10, and the engagement protrusion 62 is kept being engaged with the L-shaped outer channel 411 in the syringe connection base 40. The rib 61 on the outer cap 60 is still engaged with the assembling recess 512 in the needle cap 51 of the safety cap 50. At this time, the safety needle 10 is held in position inside the outer cap 60 to ensure the safety of using the safety needle. In addition, before the outer cap 60 is removed from the syringe connection base 40 of the safety needle 10, the resilient block 55 on the safety cap 50 does not enter into the start segment 231 of the guiding check channel 23 yet to prevent the safety needle device 1 from failure due to wrong starting position. At this time, the needle cap 51 of the safety needle 50 is mounted around the needle 30 to prevent the needle 30 from being exposed. A protective effect can be provided by the safety cap 50. Accordingly, the outer cap 60 and the safety cap 50 can provide dual protective effects during the transportation and pre-operation before the injection. The possibility of exposing the needle 30 of the safety needle 10 can be completely prevented, and a user can recognize this safety needle 10 is not used yet.

With reference to FIGS. 1 to 3 and 11, before injection, the outer cap 60 mounted around the safety needle 10 is rotated to disengage the engagement protrusion 62 on the outer cap 60 from the L-shaped outer channel 411 in the syringe connection base 40 of the safety needle 10. On the other hand, the rib on the outer cap 60 can drive the needle cap 51 of the safety cap 50 to rotate to make the resilient block 55 on the needle cap 51 move into the start segment 231 of the guiding check channel 23 from the L-shaped inner channel 215 in the front end of the needle housing 20. With such a movement, the positioning portion 53 of the safety cap 50 is kept stationary, and the needle cap 51 rotates. The resilient member 52 can gain a pre-force for rotation because of being twisted and compressed.

Figure 11:
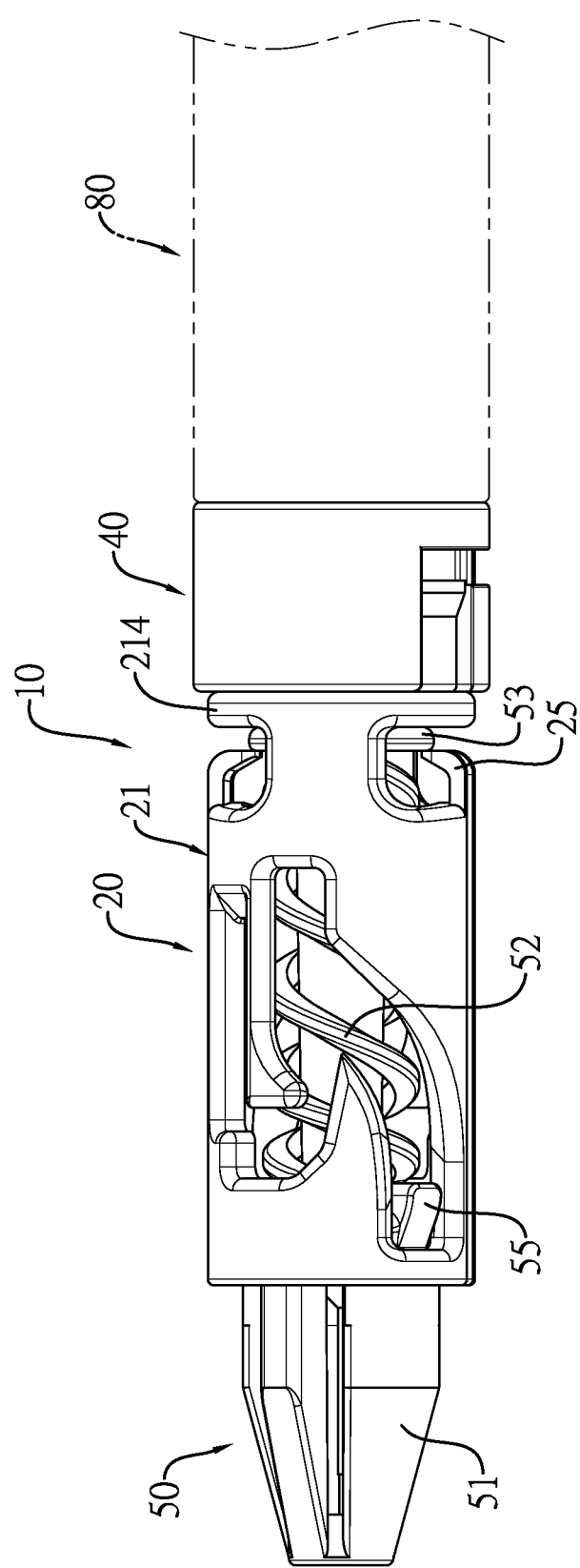
FIG. 11 is a first operational side view of the safety needle in accordance with the present invention connected with a syringe.
Figure 12:
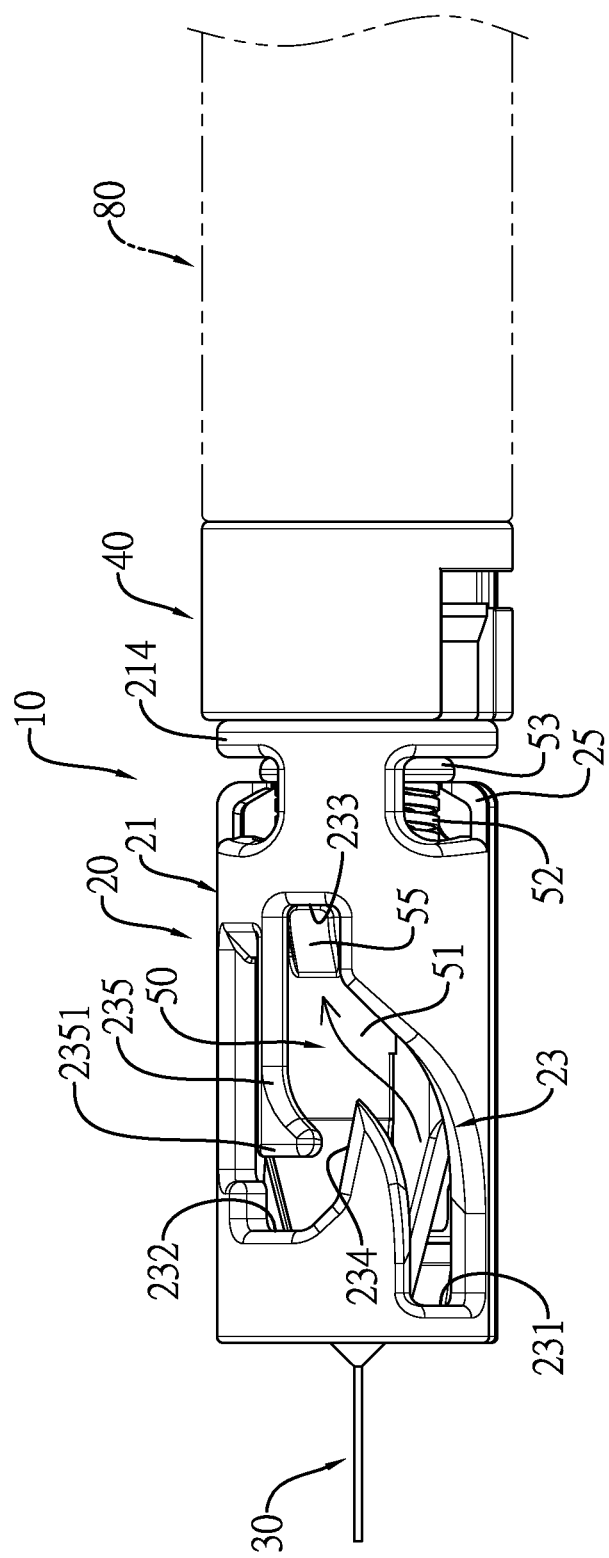
FIG. 12 is a second operational side view of the safety needle in accordance with the present invention connected with a syringe.

With reference to FIGS. 11 and 12, during the injection, a medical staff holds the syringe and pushes the front end of the safety cap 50 onto a body portion of a patient. During this process, the needle cap 51 of the safety cap 50 of the safety needle 10 still encloses the needle 30 to ensure the safety. When the front end of the safety cap 50 is in contact with the skin of the patient, the plunger of the syringe 80 is pushed, the safety cap 50 is pressed and the resilient member 52 is compressed. The needle cap 51 can be retracted into the casing 21 of the needle housing 20, and the needle 30 extends out of the front end of the needle cap 51 and is stung into the patient to inject medicine into the patient. During this process, the resilient block 55 on the needle cap 51 moves rearward from the front end of the start segment 231 of the guiding check channel 23 to the end segment 233 through the curved rear segment of the start segment. The safety cap 50 is rotated at an angle, and the needle cap 51 compresses the resilient member 52. Thus, the plunger of the syringe can be kept being pushed to inject the medicine in the syringe into the patient.

Figure 13:
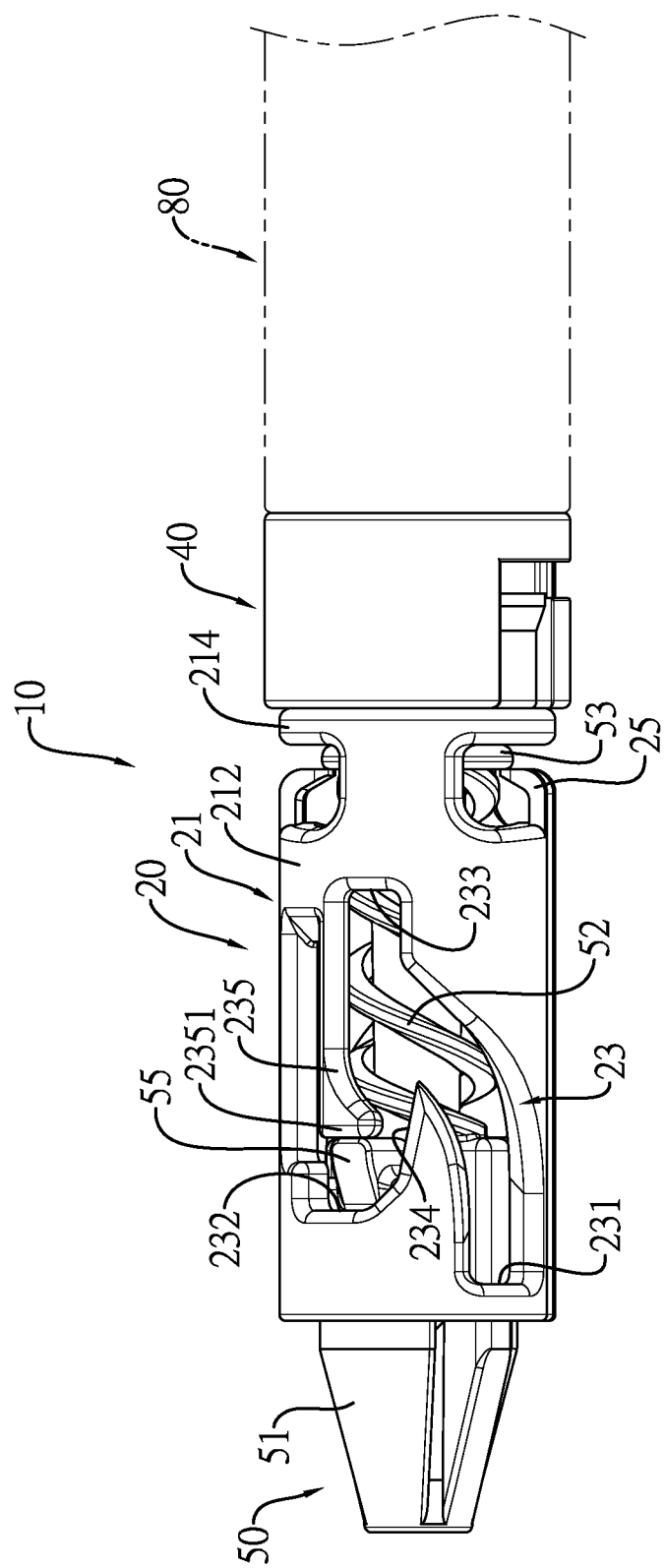
FIG. 13 is a third operational side view of the safety needle in accordance with the present invention connected with a syringe.

With reference to FIGS. 12 and 13, after the medicine is completely injected into the patient, the syringe 80 is pulled rearward, and the needle 30 of the safety needle 10 is pulled out of the patient. At this time, the resilient force provided by the resilient member 52 pushes the outer cap 51 to move out of the needle housing 20 and to enclose the needle 30 inside the needle cap 51 of the safety cap 50. Wherein, when the needle cap 51 of the safety cap 50 is pushed to move forward by the resilient force of the resilient member 52, the resilient block 55 on the needle cap 51 will move forward from the end segment 233 of the guiding check channel 23, pushes against the check tab 235, and enters the locking segment 232 through the inclined guiding segment 234. With the abutment of the check tab 235 with the resilient block 55 on the needle cap 51, the needle cap 51 can be locked in the locking segment 232 of the guiding check channel 23. The needle cap 51 cannot be moved in reverse. At this time, the needle cap 51 completely encloses the needle 30, and the safety needle 10 is locked and cannot be used again. The safety needle 10 can be recognized as used.

Accordingly, with the aforementioned safety needle and the safety needle device in accordance with the present invention, the safety cap can telescopically move and rotate relative to the needle housing, the needle housing has the guiding check channel having the check tab, and the needle cap of the safety cap has the resilient block extending into the guiding check channel. The guiding check channel comprises a start segment, a locking segment, an end segment, and an inclined guiding segment. The start segment and the locking segment are located at a front segment of the casing and are spaced from each other. The end segment is located at a rear segment of the casing, and the rear end of the start segment is connected to a middle of the end segment. The inclined guiding segment is connected between the locking segment and the front end of the end segment. The check tab on a side of the end segment extends to a side of the inclined guiding segment and the rear end of the locking segment. With the guiding effect provided by the guiding check channel having the check tab to the resilient block on the needle cap, the safety cap can axially telescopically move relative to the needle housing. The time of the needle extending out of the safety cap can be controlled, and the needle cap of the safety cap can enclose the needle with the resilient force provided by the resilient member. With the resilient block entering into the locking segment via the check tab and the inclined guiding segment, the resilient block can be limited and locked by the abutment of the check tab to prevent the resilient block from being moved in reverse. Thus, the safety cap is locked in the needle housing, and the safety needle cannot be used again.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:
1. A safety needle comprising:
 a needle housing comprising
  a casing having
  a movement space;
  an outer wall formed around the movement space and having a rear board; and
  at least one guiding check channel formed in the casing and each one of the at least one guiding check channel comprising
   a start segment located at a front segment of the casing and having a rear end;
   a locking segment located at the front segment of the casing and a side of the start segment;
   an end segment located at a rear segment of the casing and having a front end, a middle connected with the rear end of the start segment, and a check tab formed on and protruding forward from a side of the end segment opposite the start segment and having a free front end extending to a rear end of the locking segment; and
   an inclined guiding segment connected between the locking segment and the front end of the end segment, wherein the free front end of the check tab extends to a side of the inclined guiding segment; and
 a needle connection portion disposed in the movement space, protruding forward from the rear board, and having a needle assembling hole defined axially through the needle connection portion and the rear board;
 a syringe connection base connected with a rear end of the needle housing;
 a needle mounted in the needle assembling hole in the needle connection portion of the needle housing and having a front end extending out of a front end of the needle housing and a rear end extending into the syringe connection base; and
 a safety cap mounted axially moveably and rotatably in the needle housing and comprising a needle cap having a needle hole defined axially through the needle cap and at least one resilient block formed on a rear end of the needle cap and extending respectively into the at least one guiding check channel in the needle housing;

a positioning portion mounted in the movement space in the needle housing and connected with the rear board; and a resilient member connected between the needle cap and the positioning portion and mounted around the needle connection portion, wherein the safety cap is capable of axially telescopically moving in the needle housing to control the needle to extend out of the safety cap and to lock the safety cap in the needle housing, wherein the needle housing has at least one L-shaped inner channel defined in an inner surface of a front end of the casing, and extending from the front end of the casing to a position being adjacent to the start segment of one of the at least one guiding check channel; and the at least one resilient block on the needle cap of the safety cap is capable of entering respectively into the start segment of the at least one guiding check channel via the at least one L-shaped inner channel from the front end of the needle housing to make the at least one resilient block generate a pre-rotation resilient force.

2. The safety needle as claimed in claim 1, wherein
two fan-shaped recesses are defined in a front side of the rear board of the needle housing, are disposed around the needle connection portion, and are diametrically opposite each other;

at least one through channel is defined in the rear segment of the casing between the at least one guiding check channel and the rear board, and each one of the at least one through channel has a resilient hook protruding rearward from a front inner surface of the through channel and providing a limiting effect to the positioning portion of the safety cap; and the resilient member between the needle cap and the positioning portion is spiral in shape, and the positioning portion has two limiting protrusions extending respectively into the fan-shaped recesses in the rear board of the needle housing to limit a rotation range of the safety cap by the fan-shaped recesses.

3. A safety needle device comprising:
the safety needle as claimed in claim 2;
an outer cap being hollow, mounted around the safety needle and having a closed front end and an open rear end; and
a sealing film attached to the open rear end of the outer cap to seal the safety needle inside the outer cap.

4. The safety needle as claimed in claim 2, wherein
each one of the at least one guiding check channel further has an opening space located at a side of the check tab and communicating with the locking segment; and
the check tab of each one of the at least one guiding check channel has an abutment portion formed on the free front end of the check tab.

5. The safety needle as claimed in claim 2, wherein
the rear board of the needle housing has an alignment protrusion formed on a rear side of the rear board;
the needle connection portion of the needle housing has an engaging recess formed in an inner surface of a rear segment of the needle assembling hole; and
the syringe connection base comprises
a base body having a rear opening;
a front board having an alignment recess defined in a front side of the front board and corresponding to the alignment protrusion on the rear board of the needle housing;
a connection tube protruding from the front side of the front board, extending through the rear board and into the needle connection portion and having an engaging flange formed on an outer surface of the connection tube and engaged with the engaging recess; and
a needle through hole defined axially through the connection tube and the front board.

6. The safety needle as claimed in claim 1, wherein
each one of the at least one guiding check channel further has an opening space located at a side of the check tab and communicating with the locking segment; and
the check tab of each one of the at least one guiding check channel has an abutment portion formed on the free front end of the check tab.

7. The safety needle as claimed in claim 6, wherein
the needle is connected with a needle positioning plug and is mounted in the needle connection portion of the needle housing; and
the rear end of the needle is connected with a needle securing plug and is mounted in the syringe connection base.

8. The safety needle as claimed in claim 7, wherein
the rear board of the needle housing has an alignment protrusion formed on a rear side of the rear board;
the needle connection portion of the needle housing has an engaging recess formed in an inner surface of a rear segment of the needle assembling hole; and
the syringe connection base comprises
a base body having a rear opening;
a front board having two alignment recesses defined in a front side of the front board and corresponding respectively to the alignment protrusions on the rear board of the needle housing;
a connection tube protruding from the front side of the front board, extending through the rear board and into the needle connection portion, and having an engaging flange formed on an outer surface of the connection tube and engaged with the engaging recess; and
a needle through hole defined axially through the connection tube and the front board.

9. A safety needle device comprising:
the safety needle as claimed in claim 1;
an outer cap being hollow, mounted around the safety needle and having a closed front end and an open rear end; and
a sealing film attached to the open rear end of the outer cap to seal the safety needle inside the outer cap.

10. The safety needle as claimed in claim 1, wherein
the rear board of the needle housing has an alignment protrusion formed on a rear side of the rear board;
the needle connection portion of the needle housing has an engaging recess formed in an inner surface of a rear segment of the needle assembling hole; and
the syringe connection base comprises
a base body having a rear opening;
a front board having an alignment recess defined in a front side of the front board and corresponding to the alignment protrusion on the rear board of the needle housing;
a connection tube protruding from the front side of the front board, extending through the rear board and into the needle connection portion and having an engaging flange formed on an outer surface of the connection tube and engaged with the engaging recess; and
a needle through hole defined axially through the connection tube and the front board.

11. A safety needle comprising:
a needle housing comprising
 a casing having
  a movement space;
  an outer wall formed around the movement space and having a rear board; and
  at least one guiding check channel formed in the casing and each one of the at least one guiding check channel comprising
   a start segment located at a front segment of the casing and having a rear end;
   a locking segment located at the front segment of the casing and a side of the start segment;
   an end segment located at a rear segment of the casing and having a front end, a middle connected with the rear end of the start segment, and a check tab formed on and protruding forward from a side of the end segment opposite the start segment and having a free front end extending to a rear end of the locking segment; and
   an inclined guiding segment connected between the locking segment and the front end of the end segment, wherein the free front end of the check tab extends to a side of the inclined guiding segment; and
a needle connection portion disposed in the movement space, protruding forward from the rear board, and having a needle assembling hole defined axially through the needle connection portion and the rear board;
a syringe connection base connected with a rear end of the needle housing;
a needle mounted in the needle assembling hole in the needle connection portion of the needle housing and having a front end extending out of a front end of the needle housing and a rear end extending into the syringe connection base; and
a safety cap mounted axially moveably and rotatably in the needle housing and comprising
 a needle cap having a needle hole defined axially through the needle cap and at least one resilient block formed on a rear end of the needle cap and extending respectively into the at least one guiding check channel in the needle housing;
 a positioning portion mounted in the movement space in the needle housing and connected with the rear board; and
 a resilient member connected between the needle cap and the positioning portion and mounted around the needle connection portion, wherein the safety cap is capable of axially telescopically moving in the needle housing to control the needle to extend out of the safety cap and to lock the safety cap in the needle housing, wherein
the rear board of the needle housing has an alignment protrusion formed on a rear side of the rear board;
the needle connection portion of the needle housing has an engaging recess formed in an inner surface of a rear segment of the needle assembling hole; and
the syringe connection base comprises
 a base body having a rear opening;

a front board having an alignment recess defined in a front side of the front board and corresponding to the alignment protrusion on the rear board of the needle housing;
a connection tube protruding from the front side of the front board, extending through the rear board and into the needle connection portion and having an engaging flange formed on an outer surface of the connection tube and engaged with the engaging recess; and
a needle through hole defined axially through the connection tube and the front board.

12. A safety needle device comprising:
a safety needle comprising:
 a needle housing comprising
  a casing having
   a movement space;
   an outer wall formed around the movement space and having a rear board; and
   at least one guiding check channel formed in the casing and each one of the at least one guiding check channel comprising
    a start segment located at a front segment of the casing and having a rear end;
    a locking segment located at the front segment of the casing and a side of the start segment;
    an end segment located at a rear segment of the casing and having a front end, a middle connected with the rear end of the start segment, and a check tab formed on and protruding forward from a side of the end segment opposite the start segment and having a free front end extending to a rear end of the locking segment; and
    an inclined guiding segment connected between the locking segment and the front end of the end segment, wherein the free front end of the check tab extends to a side of the inclined guiding segment; and
 a needle connection portion disposed in the movement space, protruding forward from the rear board, and having a needle assembling hole defined axially through the needle connection portion and the rear board;
 a syringe connection base connected with a rear end of the needle housing;
 a needle mounted in the needle assembling hole in the needle connection portion of the needle housing and having a front end extending out of a front end of the needle housing and a rear end extending into the syringe connection base; and
 a safety cap mounted axially moveably and rotatably in the needle housing and comprising
  a needle cap having a needle hole defined axially through the needle cap and at least one resilient block formed on a rear end of the needle cap and extending respectively into the at least one guiding check channel in the needle housing;
  a positioning portion mounted in the movement space in the needle housing and connected with the rear board; and
  a resilient member connected between the needle cap and the positioning portion and mounted around the needle connection portion, wherein the safety cap is capable of axially telescopically moving in the needle housing to control the needle to extend out of the safety cap and to lock the safety cap in the needle housing;

an outer cap being hollow, mounted around the safety needle and having a closed front end and an open rear end; and a sealing film attached to the open rear end of the outer cap to seal the safety needle inside the outer cap, wherein the outer cap has
- at least one rib formed on and axially extending from an inner surface of a front segment of the outer cap; and
- at least one engagement protrusion formed on an inner surface of the open rear end of the outer cap;

the needle cap has at least one assembling recess longitudinally defined in an outer surface of the needle cap and engaged respectively with the at least one rib on the outer cap;

the syringe connection base has at least one L-shaped outer channel defined in an outer surface of the syringe connection base; and the outer cap is positioned by the engagement of the at least one engagement protrusion and the at least one L-shaped outer channel.

13. The safety needle device as claimed in claim 12, wherein the outer cap has an annular flange radially formed on an outer surface of the outer cap and attached to the sealing film.

* * * * *